US008560314B2

(12) United States Patent
Koll et al.

(10) Patent No.: US 8,560,314 B2
(45) Date of Patent: Oct. 15, 2013

(54) APPLYING SERVICE LEVELS TO TRANSCRIPTS

(75) Inventors: Detlef Koll, Pittsburgh, PA (US); Michael Finke, Pittsburgh, PA (US)

(73) Assignee: Multimodal Technologies, LLC, Pittsburgh, PA (US)

( * ) Notice: Subject to any disclaimer, the term of this patent is extended or adjusted under 35 U.S.C. 154(b) by 1284 days.

(21) Appl. No.: 11/766,784

(22) Filed: Jun. 21, 2007

(65) Prior Publication Data

US 2007/0299652 A1 Dec. 27, 2007

Related U.S. Application Data (60) Provisional application No. 60/815,689, filed on Jun. 22, 2006, provisional application No. 60/815,688, filed on Jun. 22, 2006, provisional application No. 60/815,687, filed on Jun. 22, 2006.

(51) Int. Cl.
*G10L 15/26* (2006.01)

(52) U.S. Cl.
USPC .......................................................... 704/235

(58) Field of Classification Search
USPC .......................................................... 704/235
See application file for complete search history.

(56) References Cited

U.S. PATENT DOCUMENTS

| | | | |
|---|---|---|---|
| 5,384,892 A | 1/1995 | Strong | |
| 5,434,962 A | 7/1995 | Kyojima | |
| 5,526,407 A | 6/1996 | Russell | |
| 5,594,638 A | 1/1997 | Iliff | |
| 5,669,007 A | 9/1997 | Tateishi | |
| 5,701,469 A | 12/1997 | Brandli | |
| 5,797,123 A | 8/1998 | Chou | |
| 5,809,476 A | 9/1998 | Ryan | |
| 5,823,948 A | 10/1998 | Ross, Jr. | |
| 5,835,893 A | 11/1998 | Ushioda | |

(Continued)

FOREIGN PATENT DOCUMENTS

| | | |
|---|---|---|
| EP | 0903727 A1 | 3/1999 |
| JP | 62221775 A2 | 9/1987 |

(Continued)

OTHER PUBLICATIONS

Jennifer Lai and John Vergo, "MedSpeak: Report Creation with Continuous Speech Recognition," ACM CHI 97, pp. 22-27, Mar. 1997.

(Continued)

*Primary Examiner* — Jakieda Jackson
(74) *Attorney, Agent, or Firm* — Robert Plotkin, P.C.

(57) ABSTRACT

Speech is transcribed to produce a draft transcript of the speech. Portions of the transcript having a high priority are identified. For example, particular sections of the transcript may be identified as high-priority sections. As another example, portions of the transcript requiring human verification may be identified as high-priority sections. High-priority portions of the transcript are verified at a first time, without verifying other portions of the transcript. Such other portions may or may not be verified at a later time. Limiting verification, either initially or entirely, to high-priority portions of the transcript limits the time required to perform such verification, thereby making it feasible to verify the most important portions of the transcript at an early stage without introducing an undue delay into the transcription process. Verifying the other portions of the transcript later ensures that early verification of the high-priority portions does not sacrifice overall verification accuracy.

13 Claims, 2 Drawing Sheets

(56) References Cited

U.S. PATENT DOCUMENTS

| | | |
|---|---|---|
| 5,839,106 A | 11/1998 | Bellegarda |
| 5,870,706 A | 2/1999 | Alshawi |
| 5,926,784 A | 7/1999 | Richardson |
| 5,970,449 A | 10/1999 | Alleva |
| 5,983,187 A | 11/1999 | Haddock |
| 5,995,936 A | 11/1999 | Brais |
| 6,006,183 A | 12/1999 | Lai |
| 6,041,292 A | 3/2000 | Jochim |
| 6,055,494 A | 4/2000 | Friedman |
| 6,061,675 A | 5/2000 | Wical |
| 6,112,168 A | 8/2000 | Corston |
| 6,122,613 A | 9/2000 | Baker |
| 6,122,614 A | 9/2000 | Kahn |
| 6,154,722 A | 11/2000 | Bellegarda |
| 6,182,029 B1 | 1/2001 | Friedman |
| 6,182,039 B1 | 1/2001 | Rigazio |
| 6,243,669 B1 | 6/2001 | Horiguchi |
| 6,249,765 B1 | 6/2001 | Adler |
| 6,278,968 B1 | 8/2001 | Franz |
| 6,292,771 B1 | 9/2001 | Haug |
| 6,304,848 B1 | 10/2001 | Singer |
| 6,304,870 B1 | 10/2001 | Kushmerick |
| 6,345,249 B1 | 2/2002 | Ortega |
| 6,405,165 B1 | 6/2002 | Blum |
| 6,434,547 B1 | 8/2002 | Mishelevich |
| 6,490,561 B1 | 12/2002 | Wilson |
| 6,526,380 B1 | 2/2003 | Thelen |
| 6,535,849 B1 | 3/2003 | Pakhomov |
| 6,556,964 B2 | 4/2003 | Haug |
| 6,609,087 B1 | 8/2003 | Miller |
| 6,662,168 B1 | 12/2003 | Wallach |
| 6,684,188 B1 | 1/2004 | Mitchell |
| 6,738,784 B1 | 5/2004 | Howes |
| 6,754,626 B2 | 6/2004 | Epstein |
| 6,766,328 B2 | 7/2004 | Stefanchik |
| 6,785,651 B1 | 8/2004 | Wang |
| 6,834,264 B2 | 12/2004 | Lucas |
| 6,865,258 B1 | 3/2005 | Polcyn |
| 6,915,254 B1 | 7/2005 | Heinze |
| 6,963,837 B1 | 11/2005 | Finke |
| 7,028,038 B1 | 4/2006 | Pakhomov |
| 7,031,908 B1 | 4/2006 | Huang |
| 7,043,426 B2 | 5/2006 | Roberge |
| 7,054,812 B2 | 5/2006 | Charlesworth |
| 7,184,956 B2 | 2/2007 | Frimpong-Ansah |
| 7,197,460 B1 | 3/2007 | Gupta |
| 7,216,073 B2 | 5/2007 | Lavi |
| 7,444,285 B2 | 10/2008 | Forbes |
| 7,502,741 B2 | 3/2009 | Finke |
| 7,519,529 B1 | 4/2009 | Horvitz |
| 7,555,425 B2 | 6/2009 | Oon |
| 7,555,431 B2 | 6/2009 | Bennett |
| 7,584,103 B2 | 9/2009 | Fritsch |
| 7,610,192 B1 | 10/2009 | Jamieson |
| 7,624,007 B2 | 11/2009 | Bennett |
| 7,640,158 B2 | 12/2009 | Detlef |
| 7,716,040 B2 | 5/2010 | Koll |
| 7,729,904 B2 | 6/2010 | Bennett |
| 7,844,464 B2 | 11/2010 | Schubert |
| 7,869,996 B2 | 1/2011 | Carraux |
| 7,869,998 B1 | 1/2011 | DiFabbrizio |
| 7,933,777 B2 | 4/2011 | Koll |
| 2002/0087311 A1 | 7/2002 | Lee |
| 2002/0087315 A1 | 7/2002 | Lee |
| 2002/0099717 A1 | 7/2002 | Bennett |
| 2002/0123891 A1 | 9/2002 | Epstein |
| 2002/0128816 A1 | 9/2002 | Haug |
| 2002/0156817 A1 | 10/2002 | Lemus |
| 2002/0178002 A1 | 11/2002 | Boguraev |
| 2003/0018470 A1 | 1/2003 | Golden |
| 2003/0028375 A1 | 2/2003 | Kellner |
| 2003/0065503 A1 | 4/2003 | Agnihotri |
| 2003/0069760 A1 | 4/2003 | Gelber |
| 2003/0083885 A1 | 5/2003 | Frimpong-Ansah |
| 2003/0093272 A1 | 5/2003 | Soufflet |
| 2003/0101054 A1 | 5/2003 | Davis |
| 2003/0105638 A1 | 6/2003 | Taira |
| 2003/0144885 A1 | 7/2003 | Sachdev |
| 2003/0167266 A1 | 9/2003 | Saldanha |
| 2003/0181790 A1 | 9/2003 | David et al. |
| 2003/0191627 A1* | 10/2003 | Au .................................... 704/9 |
| 2004/0019482 A1 | 1/2004 | Holub |
| 2004/0030556 A1 | 2/2004 | Bennett |
| 2004/0030688 A1 | 2/2004 | Aridor |
| 2004/0030704 A1 | 2/2004 | Stefanchik |
| 2004/0049385 A1 | 3/2004 | Lovance |
| 2004/0064317 A1 | 4/2004 | Othmer et al. |
| 2004/0078215 A1 | 4/2004 | Dahlin et al. |
| 2004/0102957 A1 | 5/2004 | Levin |
| 2004/0111265 A1 | 6/2004 | Forbes |
| 2004/0117189 A1 | 6/2004 | Bennett |
| 2004/0148170 A1 | 7/2004 | Acero |
| 2004/0172237 A1 | 9/2004 | Saldanha |
| 2004/0172245 A1 | 9/2004 | Rosen |
| 2004/0243545 A1 | 12/2004 | Boone |
| 2004/0243614 A1 | 12/2004 | Boone |
| 2004/0249667 A1 | 12/2004 | Oon |
| 2004/0267574 A1 | 12/2004 | Stefanchik |
| 2005/0065774 A1 | 3/2005 | Doganata |
| 2005/0086056 A1 | 4/2005 | Yoda |
| 2005/0086059 A1 | 4/2005 | Bennett |
| 2005/0091059 A1 | 4/2005 | Lecoeuche |
| 2005/0108010 A1 | 5/2005 | Frankel |
| 2005/0114122 A1 | 5/2005 | Uhrbach |
| 2005/0114129 A1 | 5/2005 | Watson |
| 2005/0120300 A1 | 6/2005 | Schwager |
| 2005/0144184 A1 | 6/2005 | Carus |
| 2005/0154690 A1 | 7/2005 | Nitta |
| 2005/0216443 A1 | 9/2005 | Morton |
| 2005/0228815 A1 | 10/2005 | Carus |
| 2005/0234891 A1 | 10/2005 | Walther |
| 2005/0240439 A1 | 10/2005 | Covit |
| 2005/0273365 A1 | 12/2005 | Baumgartner |
| 2005/0288930 A1 | 12/2005 | Shaw |
| 2006/0007188 A1 | 1/2006 | Reiner |
| 2006/0020466 A1 | 1/2006 | Cousineau |
| 2006/0020886 A1 | 1/2006 | Agrawal |
| 2006/0026003 A1 | 2/2006 | Cams |
| 2006/0041428 A1 | 2/2006 | Fritsch et al. |
| 2006/0041836 A1 | 2/2006 | Gordon |
| 2006/0074656 A1 | 4/2006 | Mathias |
| 2006/0089857 A1 | 4/2006 | Zimmerman |
| 2006/0129435 A1 | 6/2006 | Smitherman |
| 2006/0190263 A1 | 8/2006 | Finke |
| 2006/0195318 A1 | 8/2006 | Stanglmayr |
| 2007/0043761 A1* | 2/2007 | Chim et al. .................... 707/102 |
| 2007/0179777 A1 | 8/2007 | Gupta |
| 2007/0226211 A1 | 9/2007 | Heinze |
| 2007/0237427 A1 | 10/2007 | Patel et al. |
| 2007/0239445 A1* | 10/2007 | Kobal et al. .................... 704/235 |
| 2007/0288212 A1 | 12/2007 | Messmer et al. |
| 2007/0299652 A1 | 12/2007 | Koll |
| 2007/0299665 A1 | 12/2007 | Koll |
| 2008/0059232 A1 | 3/2008 | Iliff |
| 2008/0168343 A1 | 7/2008 | Doganata |
| 2009/0048833 A1 | 2/2009 | Fritsch |
| 2009/0055168 A1 | 2/2009 | Wu |
| 2009/0132239 A1 | 5/2009 | Finke |
| 2009/0228126 A1 | 9/2009 | Spielberg |
| 2009/0228299 A1 | 9/2009 | Kangarloo |
| 2010/0076761 A1 | 3/2010 | Juergen |
| 2010/0185685 A1 | 7/2010 | Chew |
| 2010/0299135 A1 | 11/2010 | Fritsch |
| 2011/0301982 A1 | 12/2011 | Green |

FOREIGN PATENT DOCUMENTS

| | | |
|---|---|---|
| JP | 04175966 A2 | 6/1992 |
| JP | 06168267 A2 | 6/1994 |
| JP | 2000259175 A2 | 9/2000 |
| JP | 2003022091 A | 7/2001 |
| JP | 2001272990 | 10/2001 |
| JP | 2003202895 | 7/2003 |
| JP | 2004334253 | 11/2004 |

(56) References Cited

FOREIGN PATENT DOCUMENTS

| JP | 2005107603 | 4/2005 |
| JP | 2005267358 | 9/2005 |
| JP | 2005284834 | 10/2005 |
| WO | 9416434 | 7/1994 |
| WO | 9819253 | 5/1998 |
| WO | 0054180 A1 | 9/2000 |
| WO | 0058945 | 10/2000 |
| WO | 0141126 A1 | 6/2001 |
| WO | 0233691 | 4/2002 |
| WO | 02054033 A3 | 7/2002 |
| WO | 02054385 A1 | 7/2002 |
| WO | 02071391 | 9/2002 |
| WO | 02071391 A2 | 9/2002 |
| WO | 02071391 A3 | 9/2002 |
| WO | 03034274 A1 | 4/2003 |

OTHER PUBLICATIONS

Dictaphone iChart Recognition Web Site, vwww.nuance.com/ichart, visited on Jul. 3, 2007.
Dictaphone iChart Datasheet, date unknown.
Dictaphone Speech Recognition Datasheet, date unknown.
Dictatphone Healthcare Solutions Datasheet, date unknown.
International Search Report and Written Opinion received for International Patent Application No. PCT/US2011/055494, mailed on May 4, 2012, 9 pages.
Rosenthal et al., "Voice-Enabled, Structured Medical Reporting," IEEE Intelligent Systems, vol. 13, No. 1, Jan. 1, 1998, pp. 70-73.
"Dictaphone ichart Dictate" web site, visited on Dec. 13, 2006.
"Dictaphone Powerscribe Workstation" web site, visited on Nov. 7, 2006.

* cited by examiner

APPLYING SERVICE LEVELS TO TRANSCRIPTS

CROSS REFERENCE TO RELATED APPLICATIONS

This application claims the benefit of U.S. Prov. Pat. App. Ser. No. 60/815,689, filed on Jun. 22, 2006, entitled, "Verification of Extracted Facts"; U.S. Prov. Pat. App. Ser. No. 60/815,688, filed on Jun. 22, 2006, entitled, "Automatic Clinical Decision Support"; and U.S. Prov. Pat. App. Ser. No. 60/815/687, filed on Jun. 22, 2006, entitled, "Data Extraction Using Service Levels," all of which are hereby incorporated by reference herein.

This application is related to copending and commonly-owned U.S. patent application Ser. No. 10/923,517, filed on Aug. 20, 2004, entitled "Automated Extraction of Semantic Content and Generation of a Structured Document from Speech," which is hereby incorporated by reference herein.

BACKGROUND

It is desirable in many contexts to generate a structured textual document based on human speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals.

Producing such transcripts can be time-consuming. For example, the speed with which a human transcriptionist can produce a transcript is limited by the transcriptionist's typing speed and ability to understand the speech being transcribed. Although software-based automatic speech recognizers are often used to supplement or replace the role of the human transcriptionist in producing an initial transcript, even a transcript produced by a combination of human transcriptionist and automatic speech recognizer will contain errors. Any transcript that is produced, therefore, must be considered to be a draft, to which some form of error correction is to be applied.

Producing a transcript is time-consuming for these and other reasons. For example, it may be desirable or necessary for certain kinds of transcripts (such as medical reports) to be stored and/or displayed in a particular format. Providing a transcript in an appropriate format typically requires some combination of human editing and automatic processing, which introduces an additional delay into the production of the final transcript.

Consumers of reports, such as doctors, nurses, and radiologists in the medical context, often stand to benefit from receiving reports quickly. If a diagnosis depends on the availability of a certain report, for example, then the diagnosis cannot be provided until the required report is ready. Similarly, if a doctor dictates a report of an operation into a handheld dictation device while still in the operating room, it may be desirable for a nurse to receive a transcript or other report of the dictation as soon as possible after the patient leaves the operating room. For these and other reasons it is desirable to increase the speed with which transcripts and other kinds of reports derived from speech may be produced, without sacrificing accuracy.

SUMMARY

Speech is transcribed to produce a draft transcript of the speech. Portions of the transcript having a high priority are identified. For example, particular sections of the transcript may be identified as high-priority sections. As another example, portions of the transcript requiring human verification may be identified as high-priority sections. High-priority portions of the transcript are verified at a first time, without verifying other portions of the transcript. Such other portions may or may not be verified at a later time. Limiting verification, either initially or entirely, to high-priority portions of the transcript limits the time required to perform such verification, thereby making it feasible to verify the most important portions of the transcript at an early stage without introducing an undue delay into the transcription process. Verifying the other portions of the transcript later ensures that early verification of the high-priority portions does not sacrifice overall verification accuracy.

For example, one embodiment of the present invention is a computer-implemented method comprising: (A) identifying a first semantic meaning of a first portion of a first transcript of speech; (B) assigning a first service level to the first portion of the transcript based on the first semantic meaning; (C) identifying a second semantic meaning of a second portion of the first transcript; (D) assigning a second service level to the second portion of the transcript based on the second semantic meaning; and (E) verifying the transcript in accordance with the first and second service levels.

Another embodiment of the present invention is an apparatus comprising: first meaning identification means for identifying a first semantic meaning of a first portion of a first transcript of speech; first service level assignment means for assigning a first service level to the first portion of the transcript based on the first semantic meaning; second meaning identification means for identifying a second semantic meaning of a second portion of the first transcript; second service level assignment means for assigning a second service level to the second portion of the transcript based on the second semantic meaning; and verification means for verifying the transcript in accordance with the first and second service levels.

Another embodiment of the present invention is a computer-implemented method comprising: (A) identifying a first semantic meaning of a first transcript of first speech; (B) assigning a first service level to the first transcript based on the first semantic meaning; (C) identifying a second semantic meaning of a second transcript of second speech; (D) assigning a second service level to the second transcript based on the second semantic meaning; and (E) verifying the first and second transcripts in accordance with the first and second service levels, respectively.

Another embodiment of the present invention is an apparatus comprising: means for identifying a first semantic meaning of a first transcript of first speech; means for assigning a first service level to the first transcript based on the first semantic meaning; means for identifying a second semantic meaning of a second transcript of second speech; means for assigning a second service level to the second transcript based on the second semantic meaning; and means for verifying the first and second transcripts in accordance with the first and second service levels, respectively.

Other features and advantages of various aspects and embodiments of the present invention will become apparent from the following description and from the claims.

DETAILED DESCRIPTION

Embodiments of the invention are directed to verifying a transcript of speech using multiple service levels. Service levels may, for example, correspond to required turnaround times for verification. A "high priority" service level may, for example, correspond to a relatively short turnaround time, while a "low priority" service level may correspond to another service level. As another example, the high priority service level may indicate that human verification of the corresponding text is required, while the low priority service level may indicate that human verification is not required.

The priorities of different portions of a transcript are identified. For example, the "impressions" section of a medical transcript may be identified as a high-priority section of the report, while other sections may be identified as low-priority sections. Verification of each portion of the document is performed according to that portion's service level. For example, high-priority sections (such as the "impressions" section) may be verified immediately, while low-priority sections may be verified at a later time. As another example, high-priority sections may be verified by a human, while low-priority sections may be verified by software or not at all.

Figure 1:
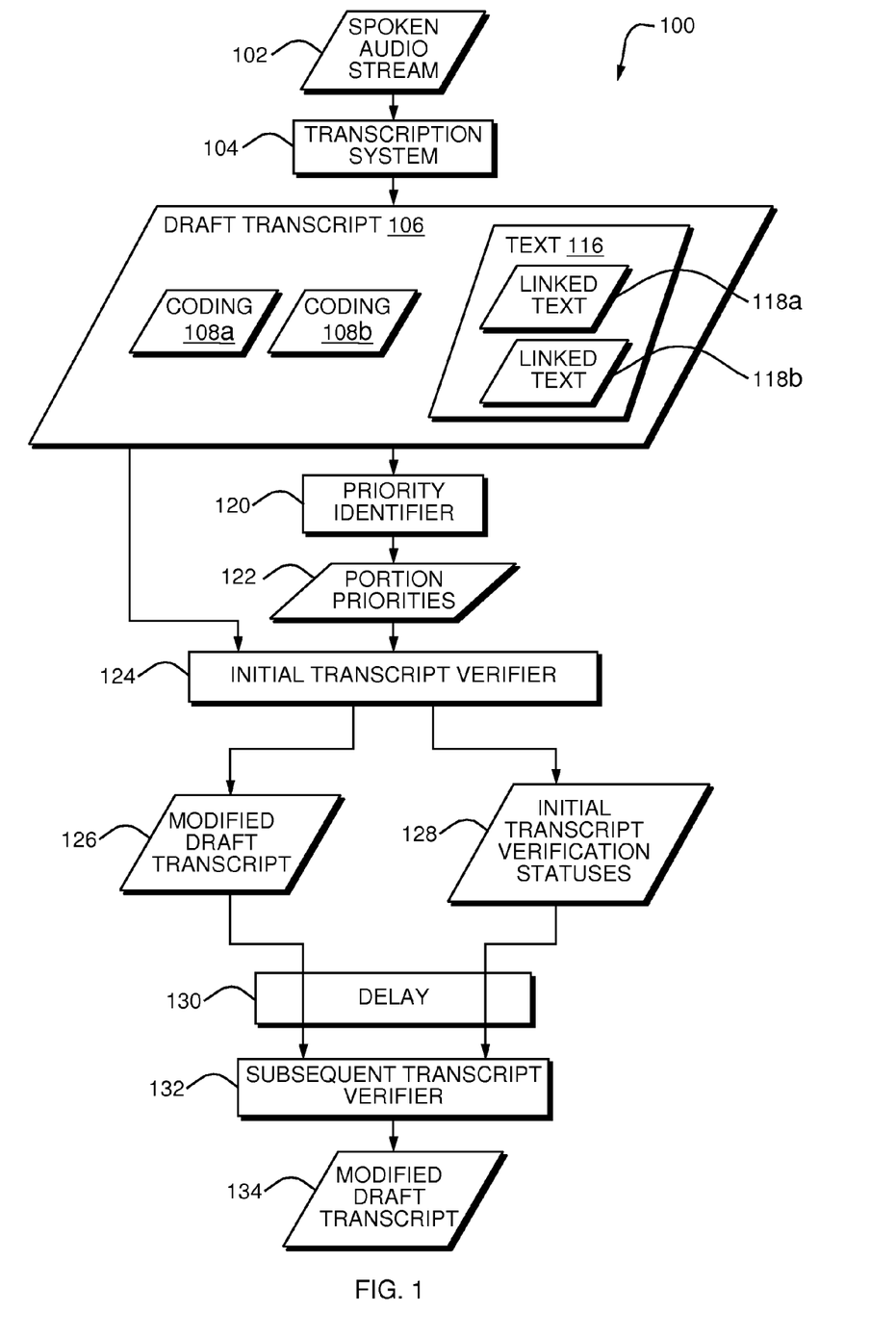
FIG. 1 is a dataflow diagram of a system for verifying a transcript of speech according to one embodiment of the present invention.
Figure 2:
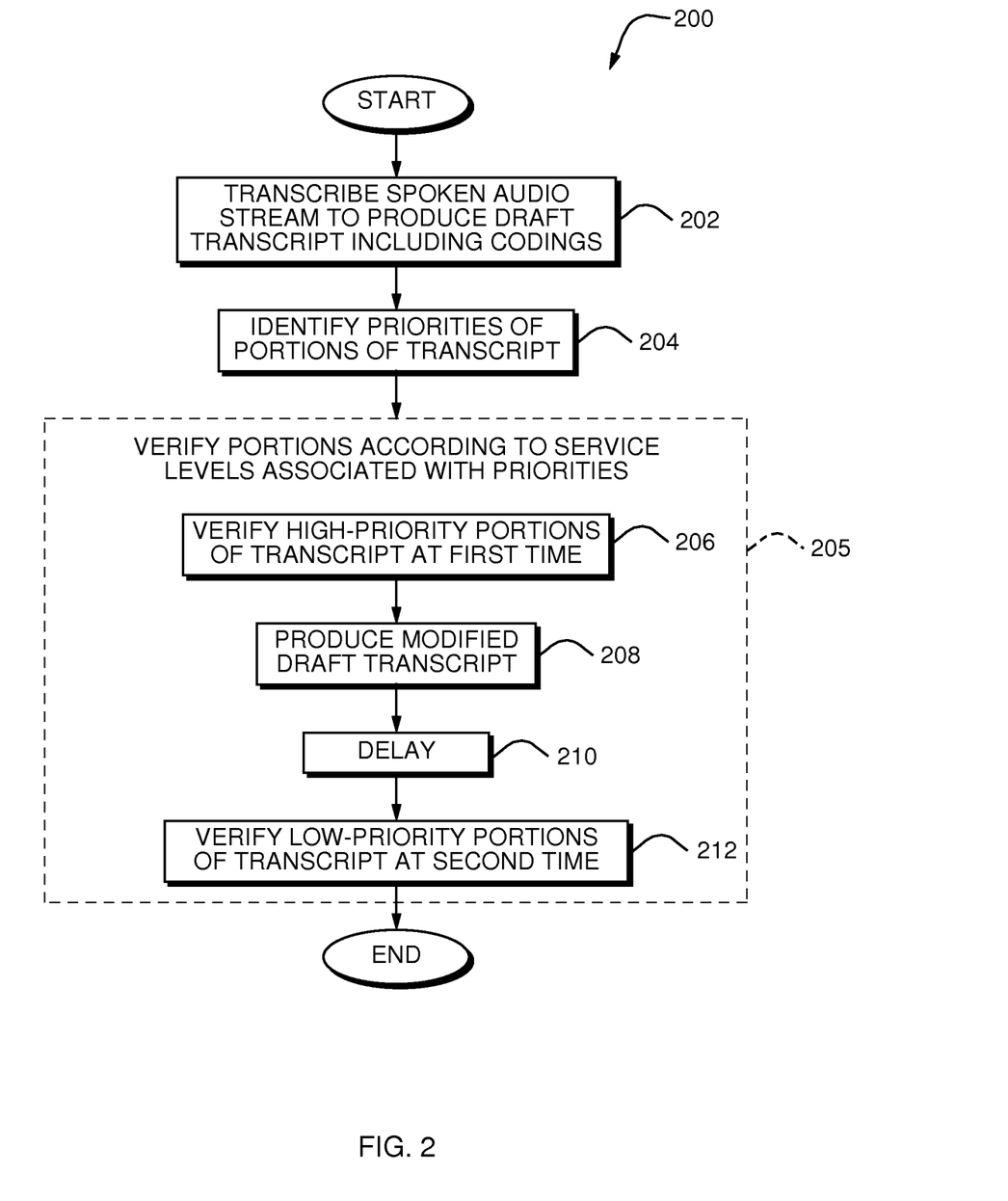
FIG. 2 is a flowchart of a method performed by the system of FIG. 1 according to one embodiment of the present invention.

More specifically, referring to FIG. 1, a dataflow diagram is shown of a system 100 for selectively verifying portions of a draft transcript 106 according to one embodiment of the present invention. Referring to FIG. 2, a flowchart is shown of a method 200 performed by the system 100 of FIG. 1 according to one embodiment of the present invention.

A transcription system 104 transcribes a spoken audio stream 102 to produce a draft transcript 106 (step 202). The spoken audio stream 102 may, for example, be dictation by a doctor describing a patient visit. The spoken audio stream 102 may take any form. For example, it may be a live audio stream received directly or indirectly (such as over a telephone or IP connection), or an audio stream recorded on any medium and in any format.

The transcription system 104 may produce the draft transcript 106 using, for example, an automated speech recognizer or a combination of an automated speech recognizer and human transcriptionist. The transcription system 104 may, for example, produce the draft transcript 106 using any of the techniques disclosed in the above-referenced patent application entitled "Automated Extraction of Semantic Content and Generation of a Structured Document from Speech." As described therein, the draft transcript 106 may include text 116 that is either a literal (verbatim) transcript or a non-literal transcript of the spoken audio stream 102. As further described therein, although the draft transcript 106 may be a plain text document, the draft transcript 106 may also, for example, in whole or in part be a structured document, such as an XML document which delineates document sections and other kinds of document structure. Various standards exist for encoding structured documents, and for annotating parts of the structured text with discrete facts (data) that are in some way related to the structured text. Examples of existing techniques for encoding medical documents include the HL7 CDA v2 XML standard (ANSI-approved since May 2005), SNOMED CT, LOINC, CPT, ICD-9 and ICD-10, and UMLS.

As shown in FIG. 1, the draft transcript 106 includes one or more codings 108, each of which encodes a "concept" extracted from the spoken audio stream 102. The term "concept" is used herein as defined in the above-referenced patent application entitled "Automated Extraction of Semantic content and Generation of a Structured Document from Speech." Reference numeral 108 is used herein to refer generally to all of the codings within the draft transcript 106. Although in FIG. 1 only two codings, designated 108a and 108b, are shown, the draft transcript 106 may include any number of codings.

In the context of a medical report, each of the codings 108 may, for example, encode an allergy, prescription, diagnosis, or prognosis. In general, each of the codings 108 includes a code and corresponding data, which are not shown in FIG. 1 for ease of illustration. Each of the codings 108 may be linked to text in the transcript 106. For example, coding 108a may be linked to text 118a and coding 108b may be linked to text 118b. Assume for purposes of example that linked text 118a is in a first section of the draft transcript 106 (such as an "impressions" section), and that linked text 118b is in a second section of the draft transcript 106 (such as a "patient history" section). Further details of embodiments of the codings 108 may be found in the above-referenced patent application entitled, "Verification of Data Extracted from Speech."

A priority identifier 120 identifies verification priorities of one or more portions of the draft transcript 106 to produce portion priorities 122 (step 204). A "portion" of the draft transcript 106 may, for example, be a single coding (such as the coding 108a or coding 108b), sentence, paragraph, or section.

In general, the priority identifier 120 identifies the priority of a portion of the draft transcript 106 by identifying a semantic meaning of the portion, and identifying the priority of the portion based on the identified semantic meaning. For example, the priority identifier 120 may be configured to assign a high priority to any "impressions" sections in the draft transcript 106 and a low priority to all other sections in the draft transcript 106.

As another example, certain portions of the draft transcript 106 may require human (rather than software-based or other automated) verification. Typically, all portions of the draft transcript 106 require human verification. Some portions, however, such as certain codings representing data which are used solely for automatic computer processing, may not be rendered to the reviewer (e.g., physician) for review and not require human verification. The priority identifier 120 may be configured to assign a high priority to any portions of the draft transcript 106 which require human verification, and to assign a low priority to all other portions of the draft transcript 106. The priority identifier 120 may identify portions of the draft transcript 106 requiring human verification in any of a variety of ways. For example, the priority identifier 120 may be configured to identify certain codings, or certain types of codings, as requiring human verification, in which case the priority identifier 120 may assign a high priority to such codings.

In general, the portions of the draft transcript 106 are verified according to service levels associated with their priorities (step 205). For example, a "high-priority" service level may be applied to portions of the transcript 106 having a high priority. Similarly, a "low-priority" service level may be applied to portions of the transcript 106 having a low priority. Since the priorities 122 of the document portions are identified based on the semantic meanings of the portions, the service levels that are applied to the portions are based on the semantic meanings of the portions.

One example of applying such service levels is illustrated by steps 206-212 in FIG. 2. More specifically, an initial transcript verifier 124 verifies, at a first time, only those portions of the draft transcript 106 which the priority identifier 120 has identified as having a high verification priority (step 206). The portion priorities 122 may, for example, include links to the corresponding portions of the draft transcript 106. The initial transcript verifier 124 may use such links to identify which portions of the draft transcript 106 have high verification priorities and to verify only those portions of the draft transcript 106. The initial transcript verifier 124 produces initial transcript verification status identifiers 128 which indicate the verification status of each of the high-priority portions of the draft transcript 106. A verification status may, for example, indicate whether the corresponding portion of the draft transcript 106 is correct or incorrect.

Any of a variety of techniques may be used to verify the high-priority portions of the draft transcript 106, examples of which may be found in the above-referenced patent application entitled, "Verification of Data Extracted from Speech." For example, the high-priority portions of the draft transcript 106 may be presented to a human reviewer, who may be the same person who dictated the spoken audio stream. In fact, the speaker of the spoken audio stream 102 may still be dictating the remainder of the spoken audio stream 102 while portions of the draft transcript 106 representing previous parts of the spoken audio stream 102 are presented to the reviewer for verification.

The verification process performed by the initial transcript verifier 124 may include correcting any portions of the draft transcript 106 that are found to be incorrect. For example, the reviewer may provide input to correct one or more portions of the draft transcript 106 presented for review. The initial transcript verifier 124 may therefore produce a modified draft transcript 126, which includes any corrections to the codings 108 or other modifications made by the initial transcript verifier 124 (step 208).

Note that the initial transcript verification status identifiers 128 and the modified draft transcript 126 may be combined. For example, portions of the modified draft transcript 126 may be tagged with their own verification statuses.

There is some delay 130 after the initial verification (step 210). The delay 130 may occur, for example, while the modified draft transcript 126 is provided to a nurse or physician for use in providing medical care.

After the delay 130, a subsequent transcript verifier 132 verifies portions of the modified draft transcript 126 other than those which were verified by the initial transcript verifier 124, thereby producing a final transcript 134 (step 212). For example, the subsequent transcript verifier 132 may verify all of the portions which were not verified by the initial transcript verifier 124. The subsequent transcript verifier 132 may use the same verification techniques as the initial transcript verifier 124. Note that although the initial transcript verifier 124 and subsequent transcript verifier 132 are illustrated as two distinct components in FIG. 1, they may be integrated into a single component (e.g., a single software program).

The techniques just described may be viewed as implementing two tiers of "service level," in which each tier corresponds to a different turnaround time requirement. The first (high-priority) tier of service level corresponds to a relatively short turnaround time, and the second (low-priority) tier of service level corresponds to a relatively long turnaround time. The priorities 122 assigned to portions of the draft transcript 106 may, however, be used to implement service levels corresponding to characteristics other than turnaround times.

For example, a first tier of service level may require the corresponding portion of the draft transcript 106 to be verified by a human, while a second tier of service level may not require human verification. For example, the second tier may require software verification or not require any verification. In this example, the method of FIG. 2 would include only steps 202-208. More specifically, step 202 would include transcribing the spoken audio stream to produce the draft transcript 106, as described above. Step 204 would include identifying priorities 122 of portions of the draft transcript 106. In this example, a high priority would indicate that human verification is required, while a low priority would indicate that human verification is not required.

Step 206 would include verifying only those portions of the draft transcript 106 having high priorities (i.e., only those portions of the draft transcript 106 requiring human verification). Such verification may, for example, be performed by providing the draft transcript 106 to a human reviewer (such as the dictating physician) for review.

The method 200 would then terminate, without verifying the low-priority portions of the draft transcript 106 because such portions have been identified as not requiring human verification. In yet another embodiment, a high service level would require verification by the dictating physician, a medium service level would require verification by a data entry clerk, and a low service level would not require any human verification.

Embodiments of the present invention have a variety of advantages. For example, transcripts of physician-dictated reports typically are not provided to nurses and others for use in patient care soon after a draft of the transcript has been produced because it has not been possible to verify the accuracy of the transcript quickly enough. As a result, draft transcripts typically are withheld until they have been verified, which can introduce a significant delay before such transcripts may be used.

One benefit of the techniques disclosed herein is that they make it possible to provide transcripts to consumers of such transcripts both quickly and with increased accuracy by limiting the amount of the transcript that is verified, at least at the outset. In particular, by limiting the verification, either initially or entirely, to high-priority portions of the draft transcript 106, the techniques illustrated in FIGS. 1 and 2 increase the accuracy of those portions of the draft transcript 106 for which accuracy is most critical, without introducing the significant delay that would otherwise be incurred by verifying the entire transcript.

Furthermore, the techniques disclosed herein do not create significant additional work for the physician or other dictator/reviewer of the transcript, and may thereby reduce the total amount of time they need to devote to performing their tasks. If, for example, the initial transcript verifier 124 presents high-priority portions of the draft transcript 106 to a physician for review immediately after the physician dictates such portions, or even while the physician is dictating such portions, the physician may verify and correct any errors in such portions more efficiently than if those portions of the transcript were provided to the physician for review an hour, day, or week later because of the switching costs involved. Furthermore, overall accuracy may be increased because the dictator/reviewer of the draft transcript 106 may have a clearer memory of the intended content of the draft transcript 106 is presented to him or her immediately after dictating it, rather than at a later time.

These techniques are particularly useful in contexts in which a transcript needs to be made available immediately to someone other than the dictator of the transcript. For example, the "impressions" section of a radiology report needs to be made available immediately for emergency room radiology studies, while the rest of the document may be completed at a later time. In order to guarantee immediate turnaround, the "impressions" section of the draft transcript 106 may be provided to the dictating physician immediately for self-correction, while leaving the remainder of the document to be corrected at a later time by professional transcriptionists.

As another example, the medication and allergy sections of a progress note may be interpreted and populated immediately in an electronic medical records (EMR) system to be available for order entry (i.e., prescription medications) and decision support at point of care. Other data elements (e.g., history of present illness) may be verified at a later time.

Another benefit of techniques disclosed herein is that they may be combined with the techniques disclosed in the above-referenced patent application entitled "Automatic Decision Support" for applying automated clinical decision support to transcripts. For example, the modified draft transcript 126 may be provided to an automated clinical decision support system, as described in the above-referenced patent application, to provide clinical decision support quickly. Such techniques may, for example, be used to provide a quick indication of whether the draft transcript 126 indicates a dangerous drug-drug allergy which requires attention by the dictating physician or other care provider. The techniques disclosed herein facilitate the provision of such rapid clinical decision support by enabling verification of high-priority portions of the draft transcript 106 to be performed soon after the draft transcript 106 is produced. If verification of such high-priority portions had to wait until all portions of the draft transcript 106 were verified, then application of automated clinical decision support to the high-priority portions would have to wait as well.

In this regard, portions of the draft transcript 106 which are necessary to provide as input a clinical decision support system may be assigned a high priority. As a result, the initial transcript verifier 124 will verify those portions of the draft transcript 106 which are necessary to provide as input to the clinical decision support system. This ensures that any desired clinical decision support can be applied to the modified draft transcript 126 produced by the initial transcript verifier 124, without incurring additional delay.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Although certain examples provided herein involve documents generated by a speech recognizer, this is not a requirement of the present invention. Rather, the techniques disclosed herein may be applied to any kind of document, regardless of how it was generated. Such techniques may, for example, be used in conjunction with documents typed using conventional text editors.

The spoken audio stream 102 may be any audio stream, such as a live audio stream received directly or indirectly (such as over a telephone or IP connection), or an audio stream recorded on any medium and in any format. In distributed speech recognition (DSR), a client performs preprocessing on an audio stream to produce a processed audio stream that is transmitted to a server, which performs speech recognition on the processed audio stream. The audio stream may, for example, be a processed audio stream produced by a DSR client.

The invention is not limited to any of the described domains (such as the medical and legal fields), but generally applies to any kind of documents in any domain. For example, although the reviewer 138 may be described herein as a physician, this is not a limitation of the present invention. Rather, the reviewer 138 may be any person. Furthermore, documents used in conjunction with embodiments of the present invention may be represented in any machine-readable form. Such forms include plain text documents and structured documents represented in markup languages such as XML. Such documents may be stored in any computer-readable medium and transmitted using any kind of communications channel and protocol.

Although certain examples described herein include only two priorities—high and low—these are merely examples of priorities and do not constitute limitations of the present invention. Rather, the techniques disclosed herein may be applied to any number of priorities defined and/or labeled in any manner. For example, there may be high, medium, and low priorities. As another examples, priorities may specify maximum turnaround times, such as one minute, one hour, and one day.

Furthermore, although in certain examples herein the high priority service level is described as providing "immediate" verification, this is not a requirement of the present invention. Rather, service levels may be defined and applied in any manner. For example, even when service levels define turnaround requirements, the highest-priority service level need not require immediate turnaround, but rather may require or allow any amount of delay.

Although certain examples disclosed herein apply different service levels to different portions of a single transcript, the same or similar techniques may be used to apply different service levels to different documents. In other words, a first (e.g., high-priority) service level may be applied to a first entire document and a second (e.g., low-priority) service level may be applied to a second entire document. The first and second documents may then be verified in accordance with their respective service levels.

For example, the transcription system 104 may transcribe a first spoken audio stream to produce a first draft transcript and apply automatic decision support to the first draft transcript using the techniques disclosed in the above-referenced patent application entitled, "Automatic Decision Support." A first service level may be associated with the first draft transcript based on the results of the automatic decision support. For example, if automatic decision support determines that the draft transcript does not include any critical errors, then a low-priority service level may be associated with the first draft transcript.

The transcription system 104 may also transcribe a second spoken audio stream to produce a second draft transcript and apply automatic decision support to the second draft transcript using the above-described techniques. A second service level may be associated with the second draft transcript based on the results of the automatic decision support. For example, if automatic decision support determines that the second draft transcript contains a critical error (such as by describing a prescription that would result in a drug-drug allergy), then a high-priority service level may be associated with the second draft transcript.

The first and second draft transcripts may then be verified in accordance with their respective service levels. For example, the second draft transcript may be presented for verification before the first draft transcript, even though the first draft transcript was transcribed before the second draft transcript, because the second draft transcript is associated with a higher service level than the first draft transcript. As one example of processing the two draft transcripts in accordance with their respective service levels, a phone call might be made immediately to the dictating physician of the second draft transcript to alert him or her to the identified error. As another example, the second draft transcript might be placed at the top of the queue of documents to which full verification is to be applied. In either case, the (low-priority) first draft transcript may be verified at a later time. Such application of different service levels to different documents shares benefits of the techniques disclosed herein for applying different service levels to different portions of a single document.

Although the verification statuses 130 may include statuses such as "correct" and "incorrect," the invention is not so limited. Rather, the verification statuses 130 may take any of a variety of forms. Further examples of the verification statuses and techniques for producing them may be found in the above-referenced patent application entitled, "Verification of Extracted Data."

Although certain individual types of service levels are described herein, such service levels are merely examples and do not constitute limitations of the present invention. For example, the above-referenced patent application entitled, "Automatic Decision Support," discloses techniques for performing real-time automatic decision support, in which decision support is applied to a transcript-in-progress while the physician (or other speaker) is still dictating the report. If the decision support system identifies a critical error or other problem requiring the immediate attention of the speaker-reviewer, the system notifies the speaker-reviewer of the problem while the report is still being dictated. Such immediate, real-time presentation of a partial transcript for review may be viewed as a service level, in comparison, for example, to service levels in which lower-priority errors are not deferred until dictation of the report is complete.

Furthermore, service levels not disclosed herein may be used in conjunction with the techniques disclosed herein. Furthermore, service levels may be combined with each other in various ways. For example, a "high-priority" service level may be applied to any portions of the draft transcript 106 which: (1) are within predetermined sections of the transcript 106; or (2) which require human verification.

The verification performed by the initial transcript verifier 124 and the subsequent transcript verifier 132 may be performed in whole or in part by a human, such as the dictator of the draft transcript 106. To facilitate such verification, the high-priority portions of the draft transcript 106 may be called out to the reviewer, such as by highlighting them or displaying them in a different color within a display of the draft transcript 106. Such a display may, for example, be displayed to the reviewer while the reviewer is dictating the contents of the transcript 106.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A method performed by at least one computer processor executing computer program instructions stored on at least one non-transitory computer-readable medium, the method comprising:
(A) identifying a first semantic meaning of a first portion of a first transcript of speech;
(B) assigning a first service level to the first portion of the transcript based on the first semantic meaning;
(C) identifying a second semantic meaning of a second portion of the first transcript;
(D) assigning a second service level to the second portion of the transcript based on the second semantic meaning; and
(E) at a processor verifying the transcript in accordance with the first and second service levels.

2. The method of claim 1, wherein (E) comprises:
(E)(1) verifying the first portion at a first time; and
(E)(2) verifying the second portion at a second time that is later than the first time.

3. The method of claim 1, wherein (A) comprises:
(A)(1) identifying a first plurality of semantic meanings of a first plurality of portions of the first transcript of speech;
wherein (B) comprises:
(B)(1) assigning the first service level to the first plurality of portions of the first transcript;
wherein (C) comprises:
(C)(1) identifying a second plurality of semantic meanings of a second plurality of portions of the first transcript;
wherein (D) comprises:
(D)(1) assigning the second service level to the second plurality of portions of the first transcript; and
and wherein (E) comprises:

(E)(1) verifying the first plurality of portions during a first time period; and (E)(2) verifying the second plurality of portions during a second time period that is later than the first time period.

4. The method of claim 1, wherein (E) comprises:

(E)(1) verifying the first portion using a human verifier.

5. The method of claim 4, wherein (E) further comprises:

(E)(2) verifying the second portion using a computer-implemented verifier.

6. The method of claim 1, wherein (A) comprises identifying a document section type of the first portion of the first transcript, and wherein (B) comprises assigning the first service level to the first portion of the transcript based on the document section type.

7. The method of claim 1, wherein (B) comprises:

(B)(1) determining whether the first portion requires verification by a human; and (B)(2) assigning the first service level to the first portion based on whether the first portion requires verification by a human.

8. An apparatus comprising at least one non-transitory computer-readable medium having computer program instructions stored thereon, wherein the computer program instructions are executable by at least one computer processor to perform a method, the method comprising:

(A) identifying a first semantic meaning of a first portion of a first transcript of speech;

(B) assigning a first service level to the first portion of the transcript based on the first semantic meaning;

(C) identifying a second semantic meaning of a second portion of the first transcript;

(D) assigning a second service level to the second portion of the transcript based on the second semantic meaning; and (E) verifying the transcript in accordance with the first and second service levels.

9. The apparatus of claim 8, wherein (E) comprises:

(E)(1) verifying the first portion at a first time; and (E)(2) verifying the second portion at a second time that is later than the first time.

10. The apparatus of claim 8, wherein (A) comprises identifying a document section type of the first portion of the first transcript, and wherein (B) comprises assigning the first service level to the first portion of the transcript based on the document section type.

11. The apparatus of claim 8, wherein (B) comprises:

(B)(1) determining whether the first portion requires verification by a human; and (B)(2) assigning the first service level to the first portion based on whether the first portion requires verification by a human.

12. A method performed by at least one computer processor executing computer program instructions stored on at least one non-transitory computer-readable medium, the method comprising:

(A) identifying a first semantic meaning of a first transcript of first speech;

(B) assigning a first service level to the first transcript based on the first semantic meaning;

(C) identifying a second semantic meaning of a second transcript of second speech;

(D) assigning a second service level to the second transcript based on the second semantic meaning; and (E) at a processor verifying the first and second transcripts in accordance with the first and second service levels, respectively.

13. An apparatus comprising at least one non-transitory computer-readable medium having computer program instructions stored thereon, wherein the computer program instructions are executable by at least one computer processor to perform a method, the method comprising:

(A) identifying a first semantic meaning of a first transcript of first speech;

(B) assigning a first service level to the first transcript based on the first semantic meaning;

(C) identifying a second semantic meaning of a second transcript of second speech;

(D) assigning a second service level to the second transcript based on the second semantic meaning; and (E) verifying the first and second transcripts in accordance with the first and second service levels, respectively.

* * * * *

UNITED STATES PATENT AND TRADEMARK OFFICE
CERTIFICATE OF CORRECTION

PATENT NO. : 8,560,314 B2  
APPLICATION NO. : 11/766784  
DATED : October 15, 2013  
INVENTOR(S) : Koll et al.

Page 1 of 1

It is certified that error appears in the above-identified patent and that said Letters Patent is hereby corrected as shown below:

On title page 3, item [56] in column 2, line 5, delete "Dictatphone" and insert -- Dictaphone --.

In the Claims

Column 10, line 48, claim 1, after "at a processor" insert -- , --.

Column 10, line 67, claim 3, after "and" delete "and".

Column 12, line 23, claim 12, after "at a processor" insert -- , --.

Signed and Sealed this  
Sixteenth Day of September, 2014

Michelle K. Lee  
*Deputy Director of the United States Patent and Trademark Office*